US005692052A

United States Patent [19]

Tanaka et al.

[11] Patent Number: 5,692,052

[45] Date of Patent: Nov. 25, 1997

[54] ENGINE NOISE CONTROL APPARATUS

[75] Inventors: Katsuyuki Tanaka, Nishio; Yoshitaka Nishio, Nagoya; Tokio Kohama, Nishio; Satoshi Kameyama, Chiryu; Kouzi Ohara, Aichi-ken; Masanori Kato, Seto, all of Japan

[73] Assignees: Nippondenso Co., Ltd., Kariya; Nippon Soken, Inc., Aichi-ken, both of Japan

[21] Appl. No.: 235,935

[22] Filed: May 2, 1994

Related U.S. Application Data

[63] Continuation-in-part of Ser. No. 142,116, Oct. 28, 1993, abandoned, which is a continuation of Ser. No. 899,533, Jun. 16, 1992, abandoned.

[30] Foreign Application Priority Data

Jun. 17, 1991 [JP] Japan .................................... 3-144970
May 21, 1993 [JP] Japan .................................... 5-142728

[51] Int. Cl.$^6$ ............................ A61F 11/06; H03B 29/00

[52] U.S. Cl. ................................................................ 381/71

[58] Field of Search ................................ 381/71, 86, 94; 181/206

[56] References Cited

U.S. PATENT DOCUMENTS 4,458,529 7/1984 Nagaishi et al. .......................... 73/204
4,506,380 3/1985 Matsui .
4,805,733 2/1989 Kato et al. .
4,878,188 10/1989 Ziegler, Jr. .
5,097,923 3/1992 Ziegler et al. .
5,119,427 6/1992 Hersh et al. .
5,146,505 9/1992 Pfaff et al. .
5,170,433 12/1992 Elliott et al. .
5,446,790 8/1995 Tanaka et al. ............................ 381/71

FOREIGN PATENT DOCUMENTS 0098594 1/1984 European Pat. Off. .
0410685 1/1991 European Pat. Off. .
0479367 9/1992 European Pat. Off. .
2531023 2/1984 France .
4041182 6/1992 Germany .
59-70868 4/1984 Japan .
62-16718 1/1987 Japan .
64-36911 2/1989 Japan .
1170754 7/1989 Japan .
02-306842 3/1991 Japan .
5209563 8/1993 Japan .
2254979 10/1992 United Kingdom .

*Primary Examiner*—Curtis Kuntz
*Assistant Examiner*—Ping W. Lee
*Attorney, Agent, or Firm*—Cushman, Darby & Cushman IP Group of Pillsbury Madison & Sutro LLP

[57] ABSTRACT

An engine rotating speed sensor detects intake sound information due to the drive of an engine. A controller generates a signal having a frequency corresponding to a desired ratio of orders based on the detected intake sound information. Further, a phase and an amplitude the signal are controlled, and so a speaker arranged in a propagation path of the intake sound of the engine generates control sound to control the intake sound due to the drive of the engine. An engine noise control apparatus which is capable of effectively reducing or waveform-reshaping a wide range of engine noise. The apparatus has an engine rotating speed sensor for detecting an engine rotating speed and a waveform generator circuit for converting a rotation pulse signal to a periodic signal having a frequency which is a predetermined multiple of the detected engine rotating speed. The output of an air flow meter is passed through a bandpass filter and a reshaping circuit to generate a control signal which is an average value of alternating current components of the output. A CPU, with reference to a map previously stored in a memory, modifies the phase and amplitude of the periodic signal with respect to an engine rotation reference signal based on the rotation pulse signal and the control signal, and outputs the modified signal as driving signals to operate speakers disposed in an intake tube and an exhaust tube for reducing noise.

4 Claims, 20 Drawing Sheets

FIG. 8

| FREQUENCY COMPONENTS (n) | | | | | | | | |
|---|---|---|---|---|---|---|---|---|
| $n_n$ | B (BLANK) | B (BLANK) | $a_{n3}$ | $a_{n4}$ | | | B (BLANK) | B (BLANK) |
| $n_{(n-1)}$ | | | | | | $a_{(n-2)(m-2)}$ | $a_{(n-1)(m-1)}$ | |
| | • • • | | | | | | | |
| $n_2$ | | | | | | $a_{2(m-2)}$ | $a_{2(m-1)}$ | $a_{2m}$ |
| $n_1$ | $a_{11}$ | $a_{12}$ | $a_{13}$ | $a_{14}$ | • • • | B (BLANK) | B (BLANK) | B (BLANK) |
| | $N_{E1}$ | $N_{E2}$ | $N_{E3}$ | $N_{E4}$ | | $N_{E(m-2)}$ | $N_{E(m-1)}$ | $N_{Em}$ |

ENGINE ROTATING SPEED →

ENGINE NOISE CONTROL APPARATUS

CROSS-REFERENCE TO RELATED APPLICATION

The present application is a continuation-in-part of U.S. patent application Ser. No. 08/142,116 filed on Oct. 28, 1993, now abandoned which is a continuation application of U.S. patent application Ser. No. 07/899,533 filed on Jun. 16, 1992, now abandoned. The disclosure of that application is incorporated herein by reference.

BACKGROUND OF THE INVENTION

1. Field of the Invention

The present invention relates to an engine noise control apparatus, and more particularly to a noise control apparatus which generates control sound in order to cancel noise or convert the noise into a more favorable tone.

2. Description of the Related Art

Intake sound and exhaust sound are two noise sources of a vehicle. Conventionally, a variety of resonators have been used to reduce intake sound, while mufflers have been used to reduce exhaust sound.

However, although these conventional noise control apparatuses mainly based on the resonance effect are effective in reducing limited noise near a resonance frequency, they do not provide sufficient noise preventing effects for engine noise which lies over a relatively wide frequency range.

SUMMARY OF THE INVENTION

It is an object of the present invention to provide an intake sound control apparatus which can control intake sound of an engine over an entire range of engine rotation.

This and other objectives are achieved by the present invention which provides an intake sound control apparatus including intake sound information sampling means for sampling intake sound information due to the drive of the engine, signal generation means for generating a signal having a frequency which is proportional to an engine rotating speed in accordance with the intake sound information sampled by the intake sound information sampling means, signal modification means for phase-controlling and amplitude controlling the signal from the signal generation means, and control sound generation means arranged in a propagation path of the intake sound of the engine for generating control signal in accordance with the signal received from the signal modification means.

The intake sound sampling means samples the intake sound information due to the drive of the engine, and the signal generation means generates the signal having the frequency which is proportional to an engine rotating speed in accordance with the intake sound information. The signal modification means phase-controls and amplitude-controls the signal from the signal generation means and the control sound generation means generates the control sound in the propagation path of the intake sound of the engine.

Furthermore, it is another object of the present invention to provide an engine noise control apparatus which is capable of effectively reducing a wide range of engine noise or converting the waveform of such engine noise.

According to the present invention as shown in FIG. 25, there is provided an engine noise control apparatus comprising means for detecting an engine rotating speed; periodic signal generation means for generating an oscillation signal having a frequency which is a predetermined multiple of the detected engine rotating speed; means for detecting pulsation components of intake air supplied to the engine; means for generating a control signal in accordance with the magnitude of the detected pulsation components of the intake air supplied to the engine; means for detecting a reference position in rotation of the engine and for outputting a reference position signal; means for modulating the phase and amplitude of the oscillation signal with respect to a reference position signal based on the engine rotating speed and the control signal, and outputting the modulated oscillation signal as a driving signal; and sound generation means disposed in at least one of intake sound and exhaust sound propagation paths of the engine for generating control sound in accordance with the driving signal.

A main frequency component causing engine intake sound and exhaust sound is a frequency which is a predetermined multiple (order) of an engine rotating speed which is defined by the number of cylinders and so on. The periodic signal generation means multiplies the engine rotating speed by a predetermined number previously determined from the number of cylinders and so on, to generate the periodic signal at the same frequency as that of problematic noise, i.e., the order of the engine rotating speed.

The periodic signal is properly modified to modulate its amplitude and phase with respect to the reference position signal based on the engine rotating speed and the control signal, and outputted to the sound generation means as a driving signal. The sound generation means, upon receiving the driving signal, generates control sound in accordance with the driving signal to cancel or reduce propagating engine intake sound and so on or convert the sound into a favorable sound waveform.

BRIEF DESCRIPTION OF THE DRAWINGS

FIG. 8 is a map of amplification factor information;

DESCRIPTION OF THE PREFERRED EMBODIMENTS

The first embodiment of the present invention is now explained with reference to the drawings.

Figure 1:
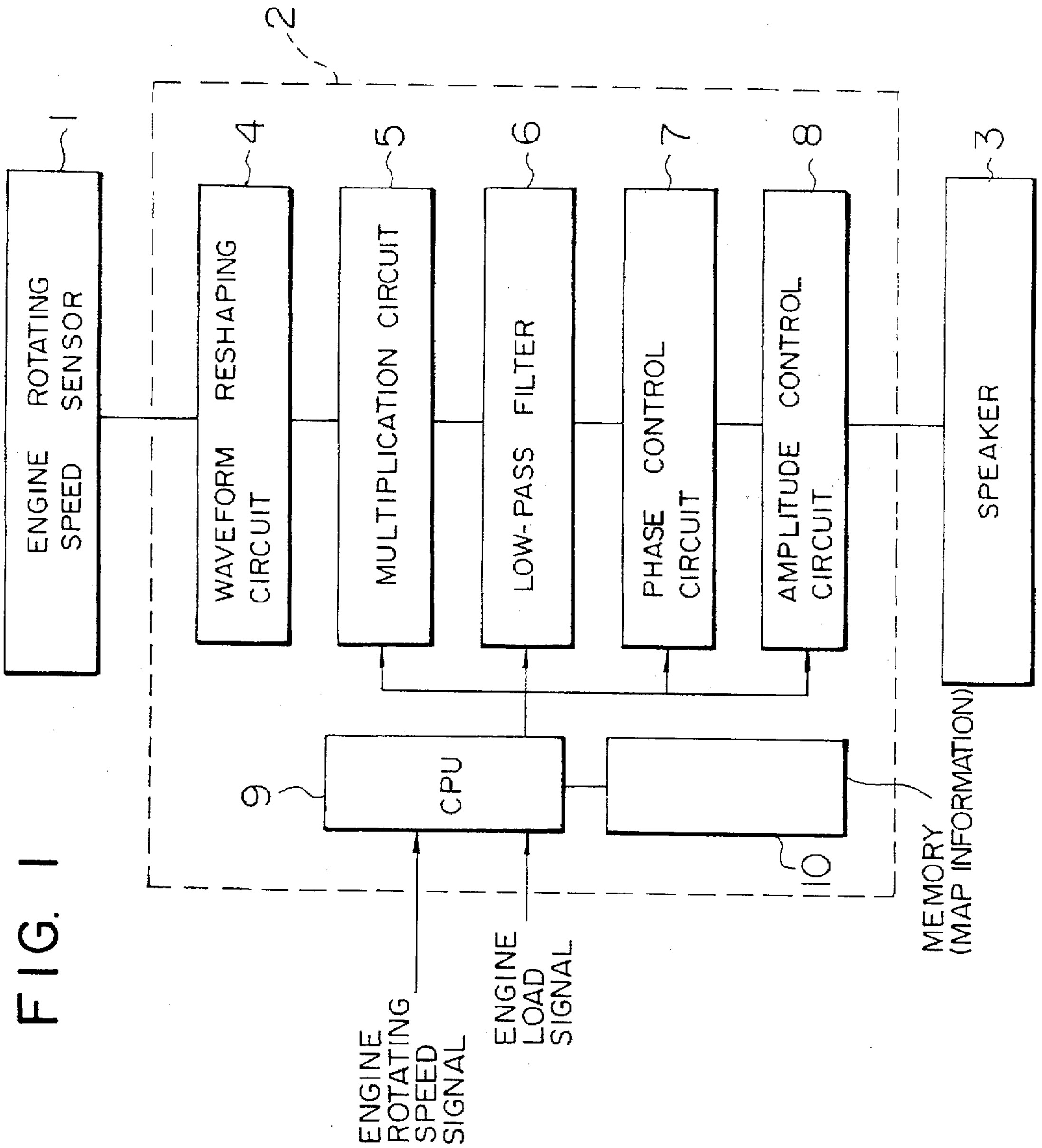
FIG. 1 is an electrical block diagram of a first embodiment of an intake sound control apparatus.

FIG. 1 shows a system block diagram of an intake sound control apparatus for an engine (internal combustion engine).

Figure 2:
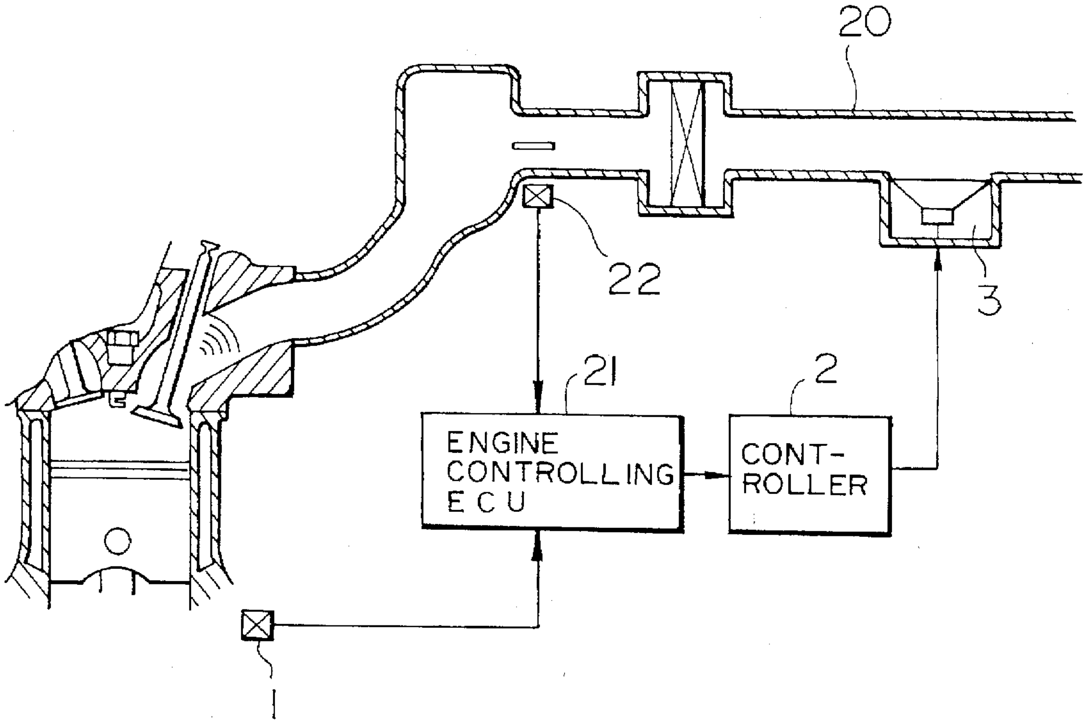
FIG. 2 is a schematic configuration of the present invention.

The intake sound control apparatus has an engine rotating speed sensor 1, a controller 2 and a speaker (controlling actuator) 3. The engine rotating speed sensor 1 produces an engine rotating speed signal (pulse signal) which represents a rotation speed of a crank shaft of the engine. In an electronically controlled engine, a signal from a rotating speed sensor for producing rotating speed information or a signal from a load sensor 22 for producing load information is normally applied to an engine controlling ECU (electronic control unit) 21 as shown in FIG. 2. This engine controlling ECU 21 may be used instead of engine rotating speed sensor 1. When the ECU 21 is used, a waveform reshaping circuit 4 shown in FIG. 1 may be omitted.

The controller 2 includes the waveform reshaping circuit 4, a multiplication circuit 5, a low-pass filter 6, a phase control circuit 7, an amplitude control circuit (amplifier) 8, a CPU 9 and a memory (storage medium) 10. The waveform reshaping circuit 4 receives the engine rotating speed signal from the engine rotating speed sensor 1 and reshapes the pulse signal. The multiplication circuit 5 is connected to the waveform reshaping circuit 4. A multiplication factor of the multiplication circuit 5 is varied in accordance with a frequency of the signal from the waveform reshaping circuit 4. Namely, the multiplication circuit 5 generates a pulse wave having a frequency which is an integer multiple of the rotating speed pulse, that is, a signal having a desired frequency to cancel the engine noise.

The low-pass filter 6 is connected to the multiplication circuit 5. The low-pass filter 6 cuts off harmonics of the signal from the multiplication circuit 5 to reshape the signal into a wave having only a fundamental frequency component of the desired frequency components. (In the first embodiment, it is close to a sine wave). The low-pass filter 6 can vary the cut-off frequency thereof by a command from the CPU 9. The cutoff frequency also varies with the frequency to be controlled and the engine rotating speed. The waveform reshaping circuit 4, the multiplication circuit 5 and the low-pass filter 6 generate a source signal having the frequency to be controlled.

The phase control circuit 7 is connected to the low-pass filter 6. It phase-controls the signal from the low-pass filter 6. The amplitude control circuit 8 controls the amplitude of the signal from the phase control circuit 7 and supplies it to the speaker 3. The signal for damping the sound is generated through the phase control circuit 7 and the amplitude control circuit 8. Both the phase control circuit 7 and the amplitude control circuit 8 are controlled by the CPU 9.

The CPU 9 receives the engine rotating speed signal and the engine load signal to detect the engine rotating speed and the engine load.

Figure 3:
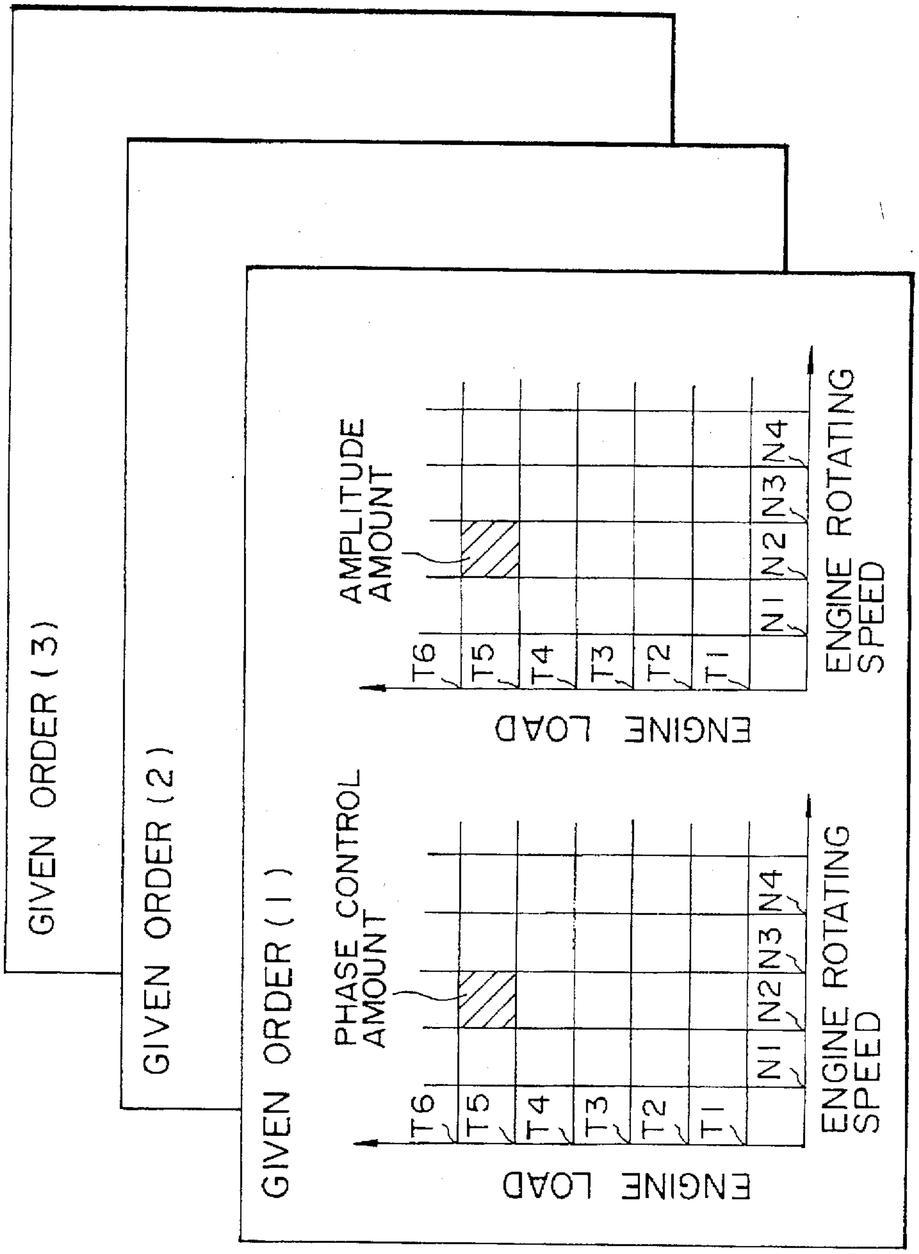
FIG. 3 is a map of phase and amplitude control amounts.

Phases of the phase control circuit 7 and amplitudes (amplification factors) of the amplitude control circuit 8 are stored in the memory 10 as map information. As shown in FIG. 3, the map information includes data of phases and amplitudes of signals for two parameters, that is, the engine rotating speed and the engine load. The map information differs from intake tube to intake tube of the engine. The map information is prepared for desired frequency components. For example, information for a second order component, which has a frequency two times an engine rotating frequency, is stored in a given order (1) map. In addition, information for a fourth order component, which has a frequency four times the engine rotating frequency, is stored in a given order (2) map.

As shown in FIG. 2, the speaker 3 is provided at a predetermined position in the intake tube system 20 of the engine. Namely, it is arranged in the propagation path of the intake sound of the engine. The speaker 3 generates control sound having a predetermined frequency components in accordance with the signal from the controller 2. Instead of the speaker 3, a vibration diaphragm may be vibrated by a piezoelectric element or it may be vibrated by changing a pressure of a pressure control chamber defined by the vibrating diaphragm using a compressor. Alternatively, the vibrating diaphragm may be arranged in a resonator so that sound generated by the vibrating diaphragm is enhanced to generate the control sound.

The CPU 9 and the memory 10 in the controller 2 may be shared with components built in the ECU 21.

Figure 4:
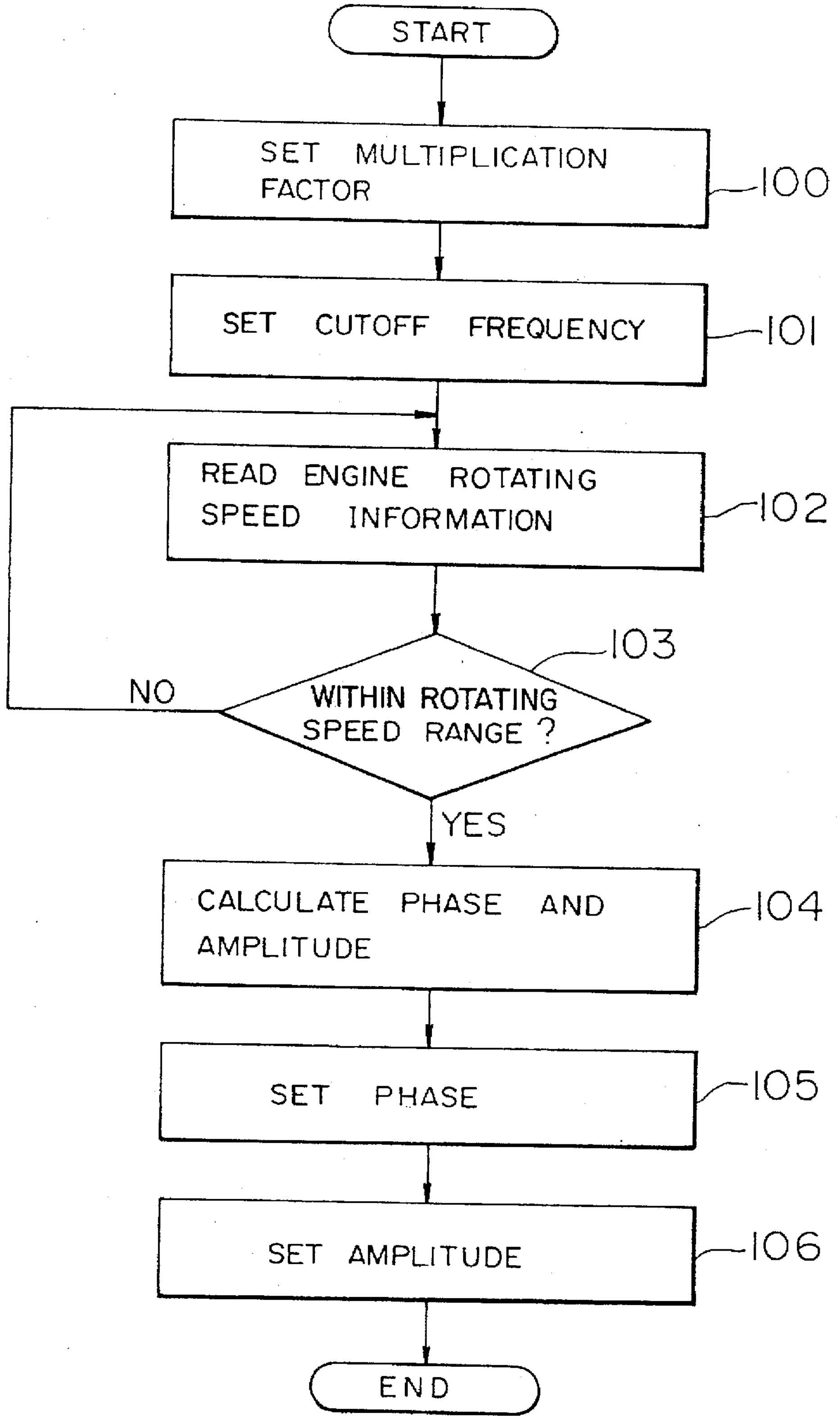
FIG. 4 is a flow chart of the first embodiment.

An operation of the intake sound control apparatus as constructed in the manner described above is now explained with reference to the flow chart of FIG. 4.

In a step 100, the CPU 9 sets the multiplication factor of the multiplication circuit 5 in order to set a desired frequency components and in a step 101 it sets a cutoff frequency of the low-pass filter 6 in order to cut off harmonics other than the frequency component to be controlled. In a step 102, the CPU 9 reads the rotation speed of the engine, and in a step 103 it determines whether the rotating speed of the engine has deviated from a rotating speed region of the map of FIG. 3. Namely, it determines whether the rotating speed of the engine has shifted from a region-defined by N1, N2, N3, . . . in FIG. 3 to an adjacent region. If the rotating speed of the engine deviates from the current rotating speed region, the CPU 9 determines, in a step 104, a phase and an amplitude using the map information in the memory 10 in accordance with the current rotating speed and load of the engine. The CPU 9 sets the phase of the phase control circuit 7 in a step 105 and the amplitude of the amplitude control circuit 8 in a step 106 based on the determined phase and amplitude. The CPU 9 repeats the above process to continue controlling the intake sound.

A highly efficient control waveform, free from the affect of rotating speed variations, is generated by generating a signal waveform having a desired frequency components based on the engine rotating speed signal. The control waveform of the desired frequency components can be generated by selecting the multiplication factor of the multiplication circuit 5 of the controller 2 under the control of the CPU 9. The phase and the amplitude of the desired frequency components at any engine rotating speed can be produced on a real time basis by using the map information stored in the memory 10.

Further, intake sound control which effects abrupt transient response control can be attained by controlling the phase control circuit 7 and the amplitude control circuit 8.

In the present embodiment, the engine rotating speed sensor 1 (intake sound information sampling means) samples the intake sound information due to the noise of the engine. The controller 2 (signal generation means and signal modifying means) generates a signal having a frequency corresponding to a desired frequency components based on the sampled intake sound information. The controller 2 phase-controls and amplitude-controls the generated signal so that the speaker 3, (control sound generation means) arranged in the propagation path of the intake sound of the engine, generates the control sound. In this manner, the intake sound of the engine can be controlled over the entire rotating speed range.

There exists a demand for quiet automobile cabins as automobile noise reduction programs progress. Among others, noise generated when the engine is rapidly accelerated is a problem. Countermeasures to the noise such as reducing the intake sound, which is at a relatively low frequency and easily propagates into the cabin, are required. The intake noise is due to the explosions occurring in the engine. In a four-cylinder engine, for example, a second order component occupies a large portion of the noise and a level thereof significantly varies with the load condition of the engine. In the present embodiment, the intake noise is reduced and modified to a sound which imparts linear feeling due to the interference of the control sound. Furthermore, the present embodiment provides a control system which can control tone.

Figure 5:
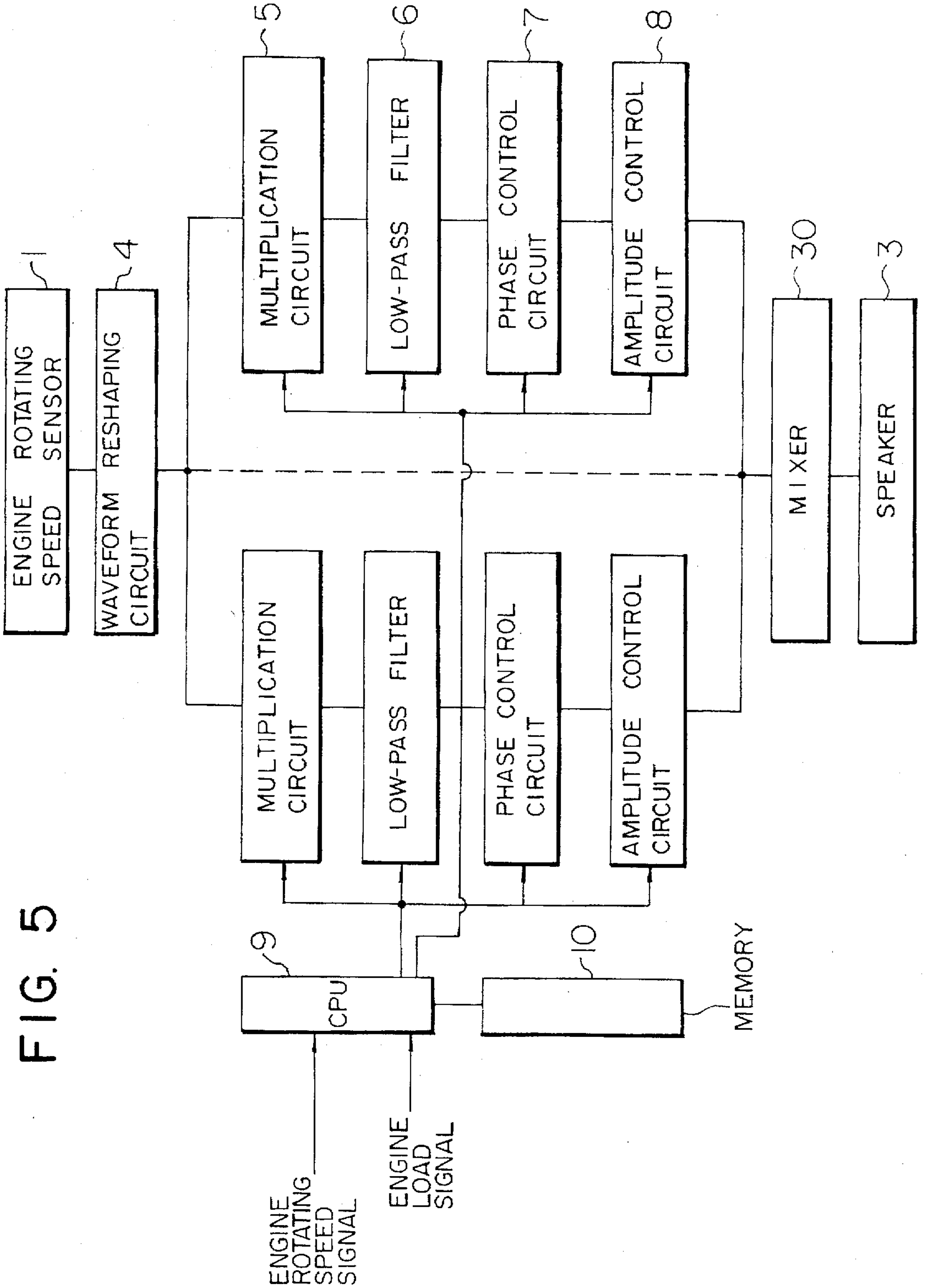
FIG. 5 is an electrical block diagram of a second embodiment.

A second embodiment is now explained with respect to differences from the first embodiment, and with reference to FIG. 5.

In the present embodiment, a plurality of the multiplication circuits 5, low-pass filters 6, phase control circuits 7 and the amplitude control circuits 8 are provided to allow parallel control of a plurality of frequency components. The control sound from the speaker 3 is controlled by a mixer 30. In this manner, the plurality of frequency components can be parallelly controlled.

A third embodiment is now explained with respect to differences from the first embodiment.

In the first embodiment, the phase and the amplitude are controlled by using map information. In the present embodiment, in addition to control using map information, the CPU 9 performs control using mathematical formulas which represent the characteristics of the intake tube systems.

The intake noise is a pulsing sound due to the explosion of the engine and it propagates in the intake tube to an intake port. A phase θ with respect to a TDC signal of a first cylinder of the engine is represented by $$\theta = 6L.Ne.n/C + KQ \quad (1)$$

where L (m) is a distance from an engine head of the intake tube (including a surge tank), or more particularly from a point of an intake value to a control point created by the speaker 3 in the intake tube; Ne (rpm) is a rotating speed of the engine; n is a control ratio of orders; C (m/s) is sound velocity; and KQ is a correction term.

The phase θ is calculated by the above formula while the amplitude is determined by using the map as is done in the first embodiment.

A fourth embodiment is now explained with reference to differences from the first embodiment.

In the first embodiment, when the engine rotating speed deviates from the rotating speed range selected by the map, the current phase and amplitude are corrected. In the present embodiment, the control amounts (phase and amplitude) are interpolated at a midpoint rotating speed of the engine rotating speeds selected by the map to obtain fine control during changes in the engine rotating speed.

Furthermore, only when the rotating speed of the engine exceeds a predetermined rotating speed range, are the phase and the amplitude calculated (interpolated). Thus, reducing the number of times the control amounts are calculated and lessening the burden on the control unit. As a result, the control unit may be shared by a control unit for controlling the engine.

Figure 6:
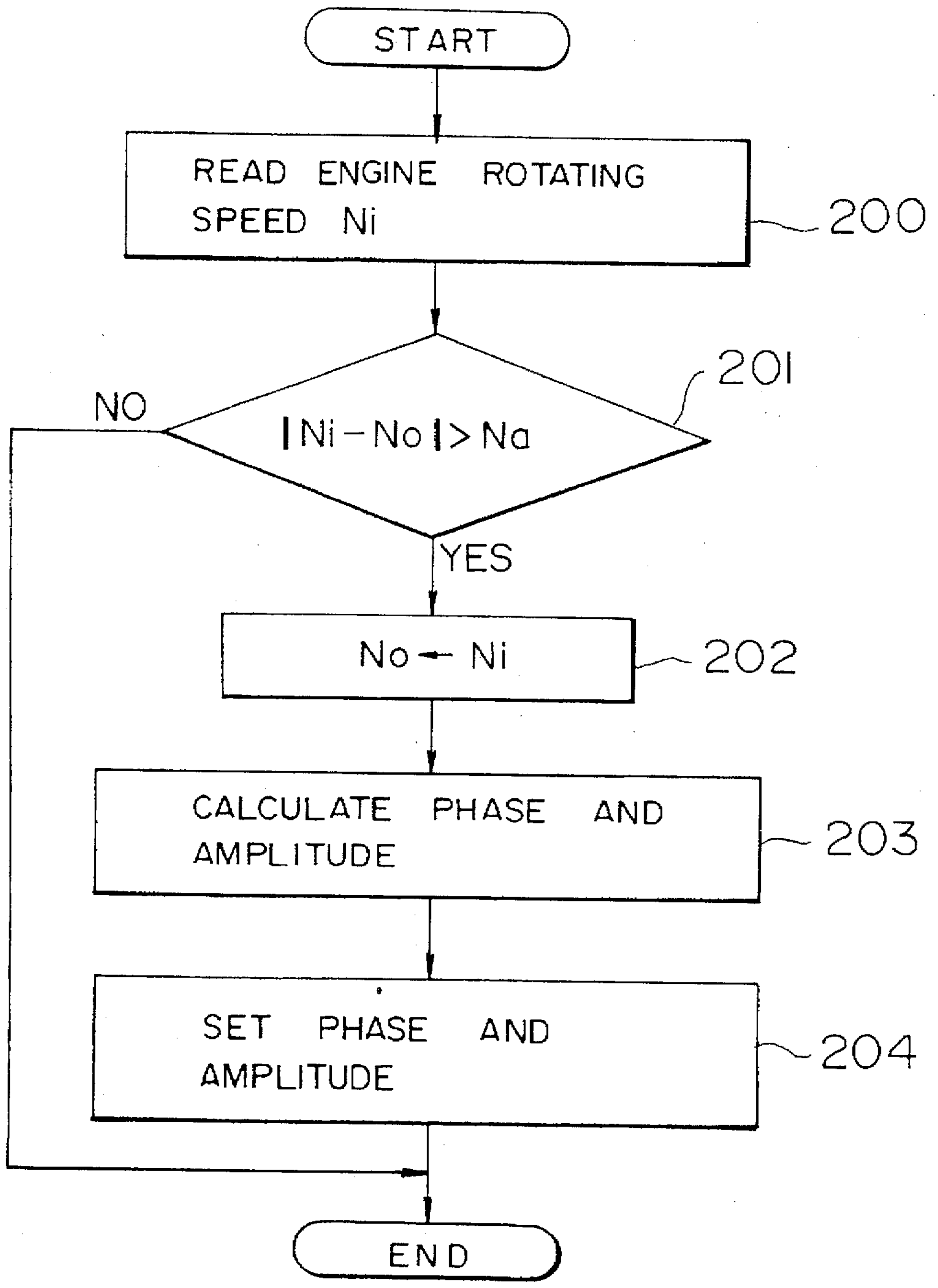
FIG. 6 is a flow chart of the second embodiment.

A flow chart which is executed by the CPU 9 is shown in FIG. 6.

In a step 200, the CPU 9 reads a current engine rotating speed $N_i$. In a step 201, it calculates an absolute value of a difference from a previous control rotating speed $N_o$ and compares it with a predetermined value (rotating speed variation range) $N_a$. If $|N_i - N_o| > N_a$, the CPU 9 sets the current engine rotating speed $N_i$ as the control rotating speed $N_o$ and stores it in a step 202. In a step 203, the CPU 9 calculates a phase and an amplitude for the control rotating speed $N_o$, and sets them in a step 204. The phase and the amplitude for the engine rotating speed are determined by using the prestored map information and mathematical formulas which have been set for each of the intake tubes of the engine.

The affect of a changing engine rotating speed is reduced and the tracking of the engine rotating speed is maintained by the active noise control system of the present invention. The active noise control attaines a finer control over changes in engine rotating speed due to the interpolation of control values. Furthermore, the present invention reduces the burden on the control unit by reducing the number of times the control amounts are calculated.

Figure 7:
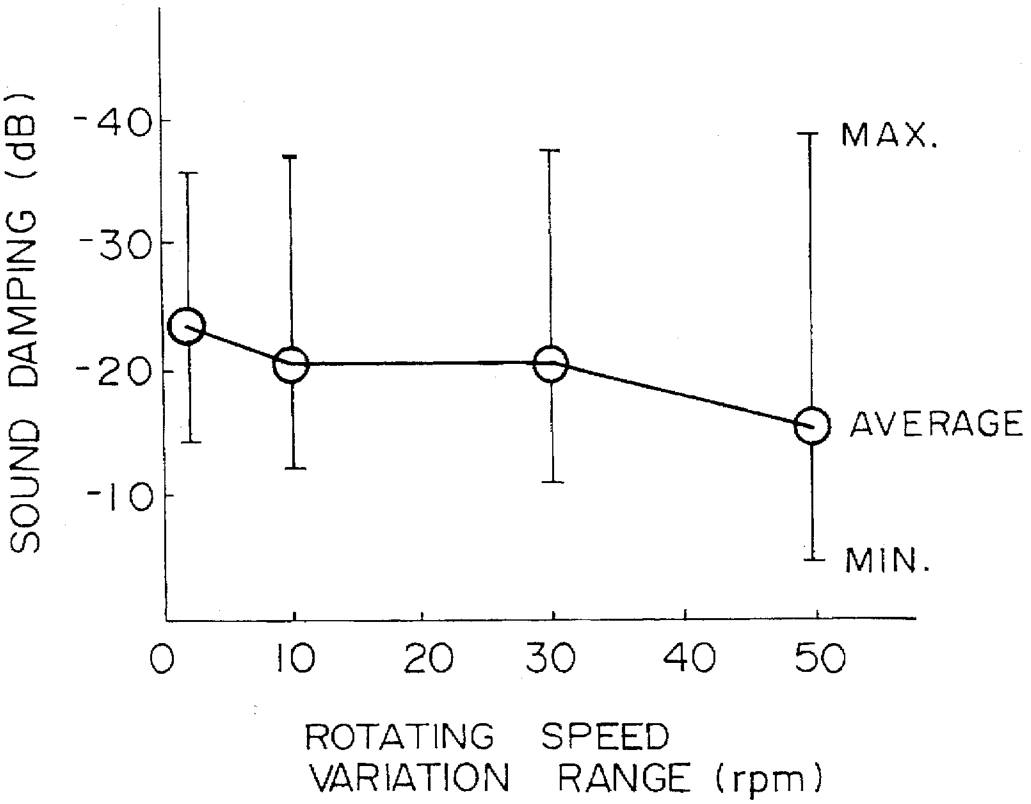
FIG. 7 is a graph of the relation between a variation of the rotating speed and the amount of sound damping.

As shown in FIG. 7, the inventors of the present invention experimented to determine a relation between the rotating speed variation range and noise damping when the engine rotation speed was rapidly accelerated from 2800 rpm to 5500 rpm in 15 seconds. In FIG. 7, the abscissa represents the rotating speed variation range and the ordinate represents the sound damping at an end of an opening of the inlet tube of the automobile. Sound damping of 20 dB or greater is attained at a rotating speed variation range 10 rpm. The sound damping of 20 dB at the end of the opening of the intake tube offers a sound damping effect which a crew of the automobile can confirm.

It has been thus proved that the rotating speed variation range ($N_a$ in FIG. 4) is preferably 10 rpm.

A fifth embodiment is now explained with respect to differences from the first embodiment.

In the first embodiment, the map information of the plurality of ratios of orders over the entire rotating speed range are provided. In the present embodiment, the phases for respective frequencies and the amplitudes for specific orders at the respective rotating speeds are stored. As a result, effective tone control with less information is attained.

FIG. 8 is a map of amplification factor information. The abscissa represents an engine rotating speed $N_E$ and the ordinate represents a ratio n of orders for the rotating speeds. The map of FIG. 8 indicates that an amplification factor (the amplitude) of the control signal having a desired frequency components at a given rotating speed is equal to a. For example, when the rotating speed of the engine is $N_{E1}$ and the frequency component is $n_1$, the amplification factor is $a_{11}$. When the frequency component remains at $n_1$ but the rotating speed changes to $N_{E2}$, the amplification factor changes to $a_{12}$. For a rotating speed therebetween, the amplification factor a is linearly interpolated.

Figure 9:
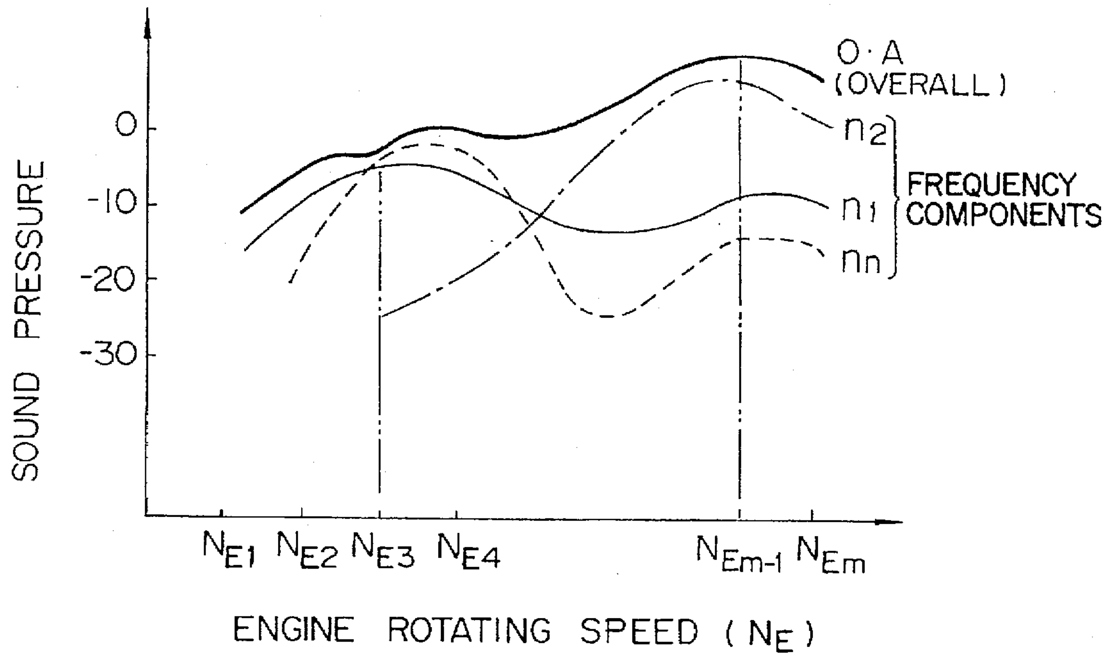
FIG. 9 is a graph of the relation between a rotating speed of an engine and sound pressure.

FIG. 9 shows analysis of the frequency component. As seen from FIG. 9, the intake sound characteristics of the intake systems differ from engine to engine, and the engine rotating speeds at which the ratios of orders $n_1$, $n_2$, $n_3$, . . . appear to peak vary in a wide range. It is thus seen from FIG. 9 that the frequency component which affects the overall values, changes with the rotating speed of the engine. When the frequency component is $n_1$, the peak appears around rotating speed $N_{E3}$ and when the frequency component is $n_2$, the peak appears around the rotating speed $N_{EM-1}$. Clearly, the ratio of orders significantly affects the overall values. Thus, the control of the intake sound is attained by controlling the frequency components.

The FIG. 8 map information on amplification factors is obtained based on the analysis of the frequency components of FIG. 9. In the map of FIG. 8, non-information areas (shown by B in FIG. 8) indicate that the sound of the particular frequency component at the particular rotating speed does not contribute to the overall level or the tone. Here, the intake sound would not be affected even if the particular frequency component could be controlled. Accordingly, the sound to be controlled may be only for a single frequency component instead of the plurality of frequency components of the engine explosion. In this case, the volume of map information may be reduced. In addition, the amplification factor information of FIG. 6 is for that under a full load condition at a given frequency component and given rotating speed. Since the engine load varies, the CPU 9 calculates the current load from time to time based on a negative pressure of the intake air of the engine and a throttle aperture as is done in electronically controlled engines. The CPU 9 determines a final amplification factor from a relationship between the calculated load and a full load.

Figure 10:
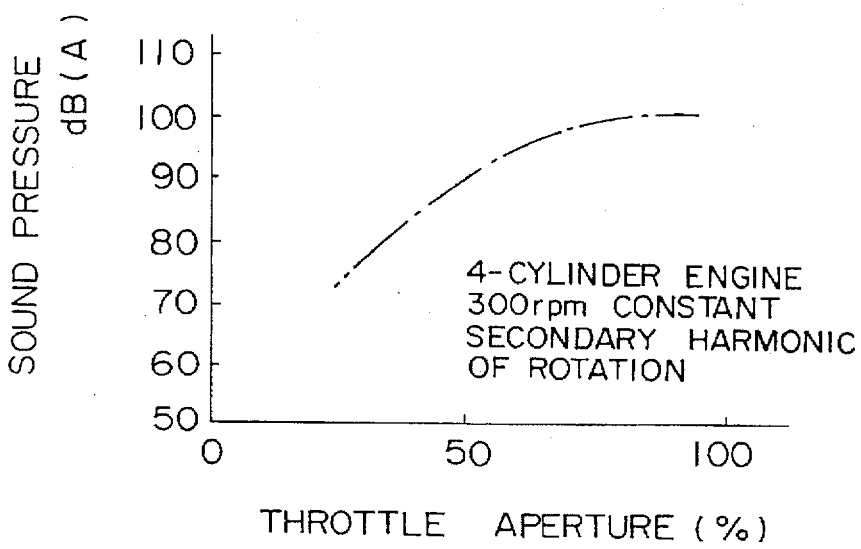
FIG. 10 is a graph of the relation between a throttle opening and sound pressure.

Specifically, as shown in FIG. 10, the intake sound is maximum when the throttle value aperture is large, that is, at the full load, and the intake sound reduces as the throttle value aperture reduces. Thus, the final amplification factor is determined based on a table of a correction amount w at a throttle value aperture α (that is, (sound pressure at a given load)/(sound pressure at the full load)) as shown in FIG. 11.

When the throttle aperture is small, that is, when the intake sound is low, control may not be necessary. For example, no control is performed when the throttle aperture is smaller than the aperture which causes a sound pressure 10 dB lower than a full load. Therefore, the chart of FIG. 11 may be simplified.

Figure 11:
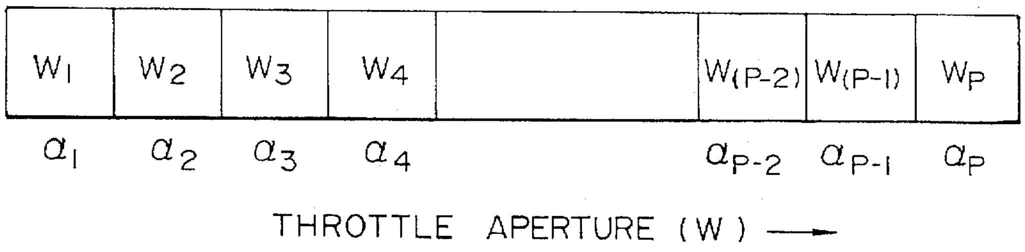
FIG. 11 is a map of throttle apertures.
Figure 12:
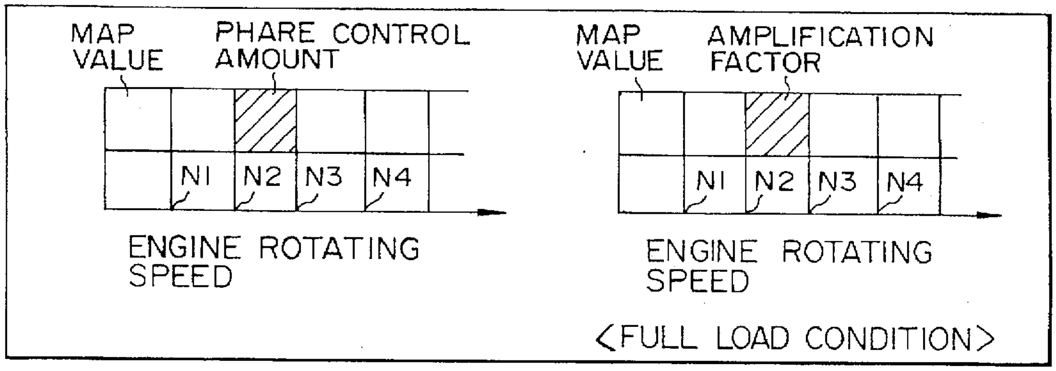
FIG. 12 is a map of phase and amplitude control amounts.

In the map information of FIG. 3, the engine load of the ordinate may be only full load as shown in FIG. 12, and a coefficient may be multiplied thereto in accordance with the table of FIG. 11.

The amplitude control method has thus been described.

Figure 13:
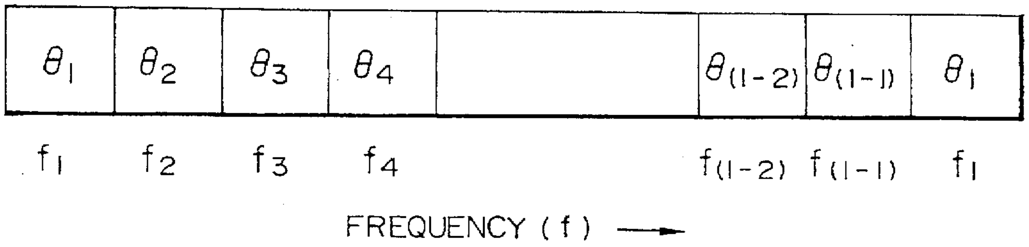
FIG. 13 is a map of frequencies.

The phase θ, which is another control factor, may be determined from map information, as in FIG. 8. However, in the present embodiment the phase θ at a given frequency f is given as table information as shown in FIG. 13. The frequency f is determined by the rotating speed $N_E$ and the of orders n of orders, and it is represented by $$f = N_E \cdot n / 60 \quad (2)$$

where $N_E$ is in rpm and f is in $H_2$.

Since the phase θ differs from intake system to intake system and the intake sound is due to the explosions in the engine, the phase θ for the frequency f is determined for the position of the speaker 3 with respect to the TDC signal of the first cylinder of the engine. In this manner, phase control is attained without map information of the phase θ for the ratio n so long as the information at the frequency f is given. When amplitude control is required (FIG. 8) and the rotating speed $N_E$ and the ratio n at which the amplitude information is written are determined, the frequency f is determined from the formula (2) and the phase is determined from FIG. 13.

By determining the phase and the amplitude in this manner, the amount of information needed to control intake noise is materially less than the method of having control amounts of the plurality of frequency components for the entire rotating speed range and the entire load range. The access time required for the control is also reduced, and control at higher speeds is performed with greater accuracy. Efficient intake sound control is attained using less information by storing the phase control signal for the frequencies and the amplification factor information of the specified frequency components for the rotating speeds instead of storing the map information the plurality of ratios of over the entire rotating speed range.

Figure 14:
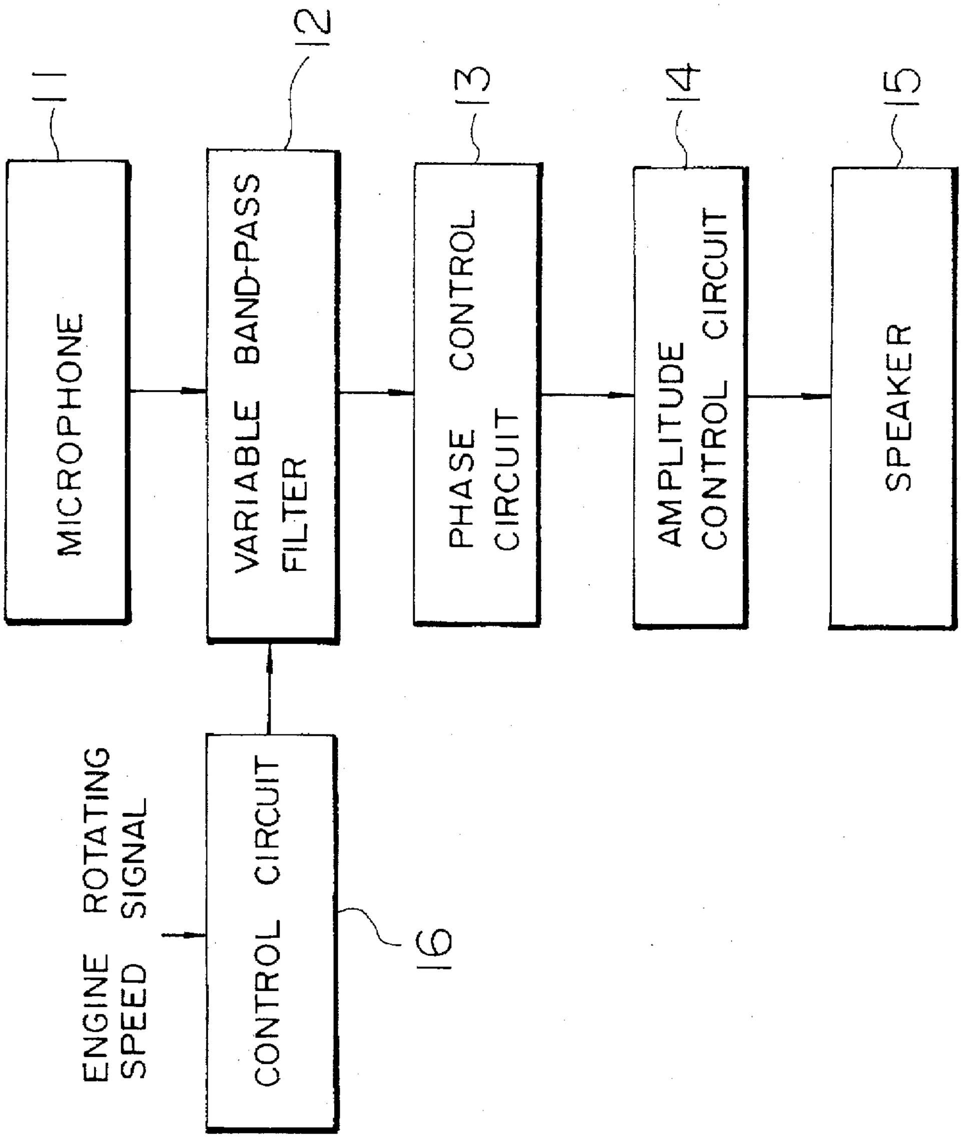
FIG. 14 is an electrical block diagram of a sixth embodiment of the intake sound control apparatus according to the present invention.

A sixth embodiment is now explained with reference to FIG. 14.

In the above embodiments, the engine rotating speed sensor 1 samples the intake sound information due to the drive of the engine. In the present embodiment, the intake sound is directly detected by a microphone 11.

The microphone 11 is arranged at a position to detect the intake sound of the engine and it converts the intake sound to an electrical signal. A variable bandpass filter 12 which can vary a pass band is connected to the microphone 11. The variable band-pass filter 12 passes only those parts of the signals from the microphone 11 which are in a preset band. A phase control circuit 13, an amplitude control circuit 14 and a speaker 15 are connected in this sequence to the variable band-pass filter 12. A control circuit 16 receives the engine rotating speed signal to detect the engine rotating speed. The control circuit 16 calculates a center pass band frequency of the variable band-pass filter 12 from the engine rotating speed and a target order by using the formula (2). The control circuit 16 then sets a predetermined width centered at the calculated center frequency as the pass band of the variable band pass filter 12.

An operation of the present embodiment is described below.

The control circuit 16 sets the pass band of the variable band-pass filter 12 based on the rotating speed of the engine and the target order. The microphone 11 detects the intake sound of the engine, the variable band-pass filter 12 extracts only the signal which has the desired ratio of orders, the phase control circuit 13 controls the phase, the amplitude control, circuit 14 controls the amplitude, and the speaker 15 generates the control sound.

In the present embodiment, the microphone 11 (intake information sampling means) samples the intake sound due to the drive of the engine, the variable bandpass filter 12 and the control circuit 16 (signal generation means) extract the signal having the frequency corresponding to the desired ratio of orders from the intake sound from the microphone 11, the phase control circuit 13 and the amplitude control circuit 14 (signal modifying means) phase-control and amplitude-control the filtered signal, and the speaker 15 (control sound generation means) generates the control sound.

Wave reshaping incorporated in a seventh, embodiment is now explained.

In previous embodiments, the high frequency components are cut off by the low-pass filter 6 of FIG. 1 to reshape the sine wave. In an alternative method, when a square or rectangular wave having a duty factor of 50 is used, a difference in the shape between that wave form and a sine wave having the same period can be uniquely defined. Thus, the sine wave reshaping may be attained by correcting a difference from the sine wave of the same period.

A method which does not use the multiplication circuit 5 is now explained as an eighth embodiment.

In the eighth embodiment, a crank angle signal is input instead of the engine rotating speed, and a frequency divider is used instead of the multiplication circuit 5.

[Ninth Embodiment]

Figure 15:
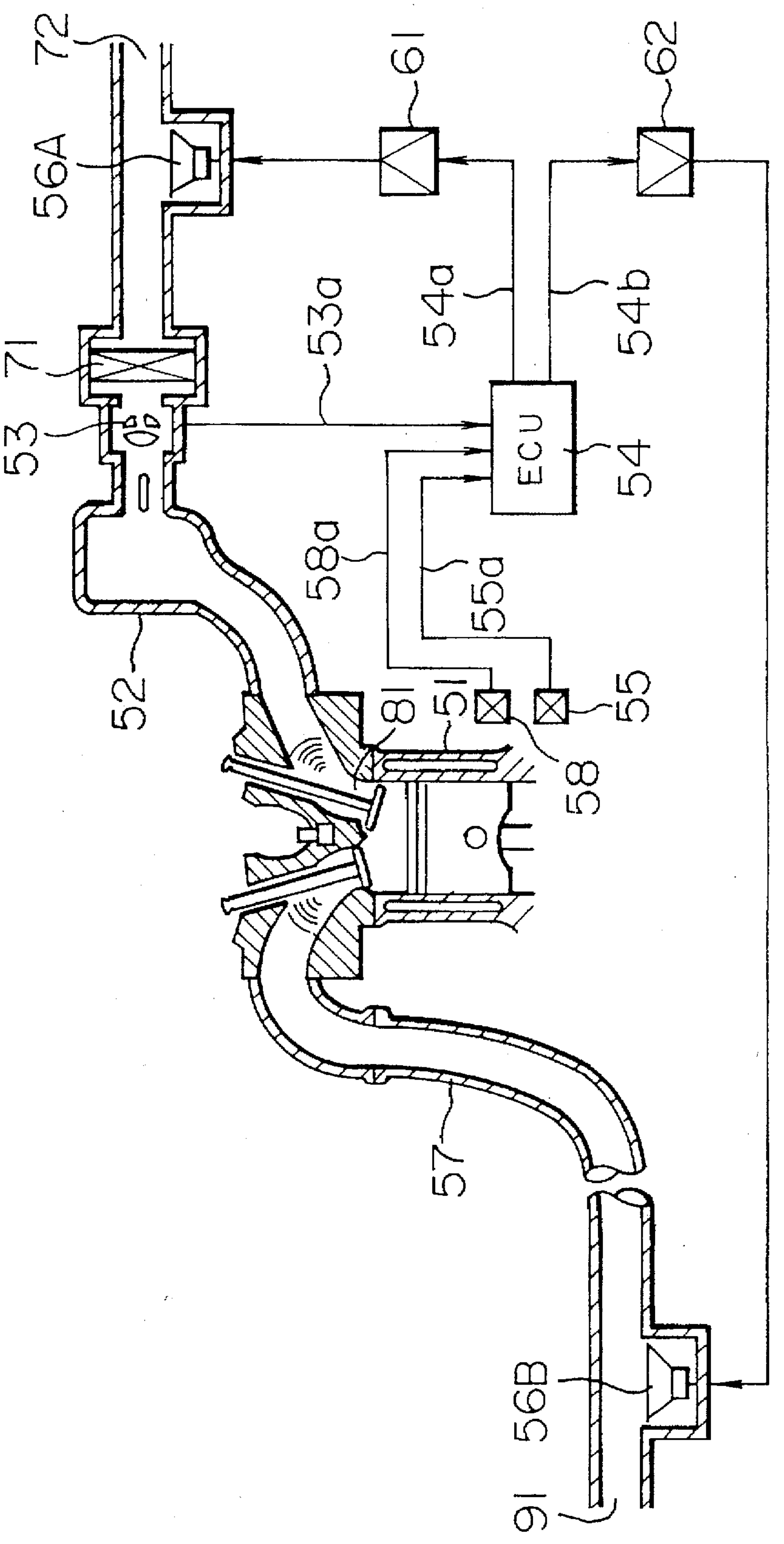
FIG. 15 is a diagram showing the whole configuration of a noise control apparatus.

FIG. 15 shows the configuration of an engine noise control apparatus. An air flow meter 53 of a known structure using a hot-wire is disposed in an intake tube extending from an intake port 81 of an engine cylinder 51 at a location downstream of an air cleaner 71. An output signal 53*a* of the air flow meter 53 is inputted to an electronic control unit (ECU) 54. This ECU 54 is also supplied with a rotation pulse signal 55*a* corresponding to an engine rotating speed from a known engine rotating speed sensor 55 as well as a reference position signal 58*a* corresponding to an explosion timing of the engine from a known engine rotation reference position sensor 58.

The ECU 54 not only controls an electronic fuel injection (EFI) and so on, but also generates driving signals 54*a*, 54*b* from the signals 53*a*, 55*a*, 58*a*, for damping intake sound and exhaust sound by a procedure, later described. These driving signals 54*a*, 54*b* are respectively outputted through amplifiers 61, 62 to a speaker 56A which is placed in the intake tube 52 near an intake opening 72 for serving as an actuator for controlling intake sound and a speaker 56B which is placed in an exhaust tube 57 near an exhaust opening 91 for serving as an actuator for controlling exhaust sound.

Figure 16:
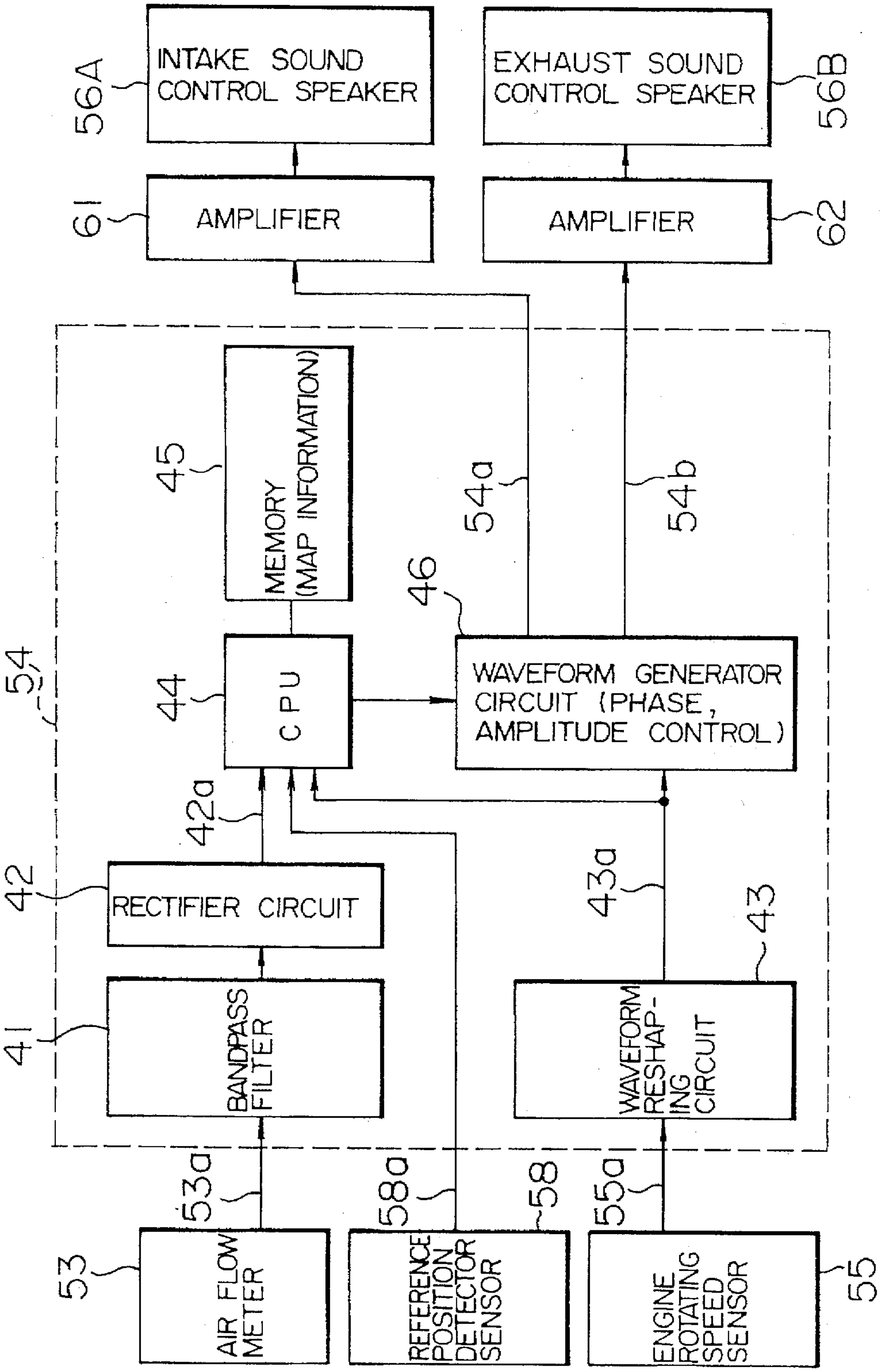
FIG. 16 is a block diagram showing the configuration of an electronic control unit.
Figure 19:
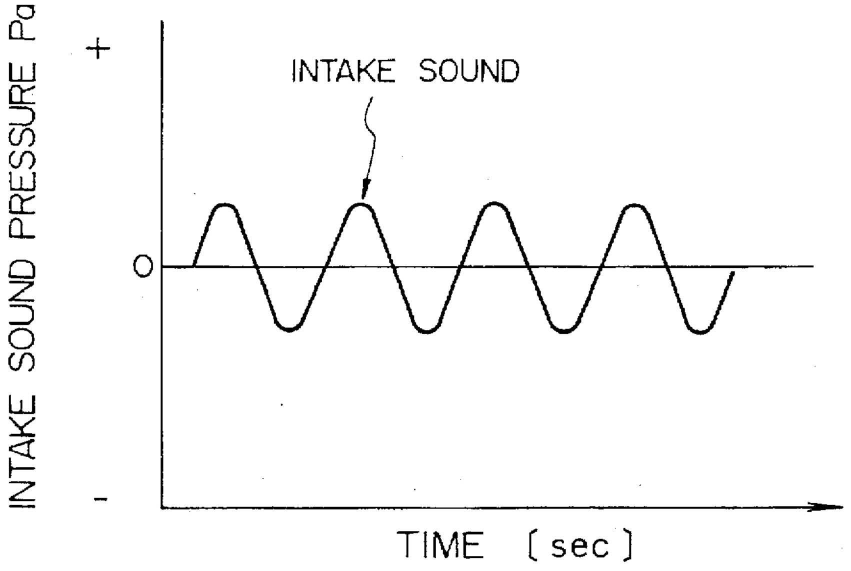
FIG. 19 is a graph showing changes in intake sound pressure with respect to the time.
Figure 20:
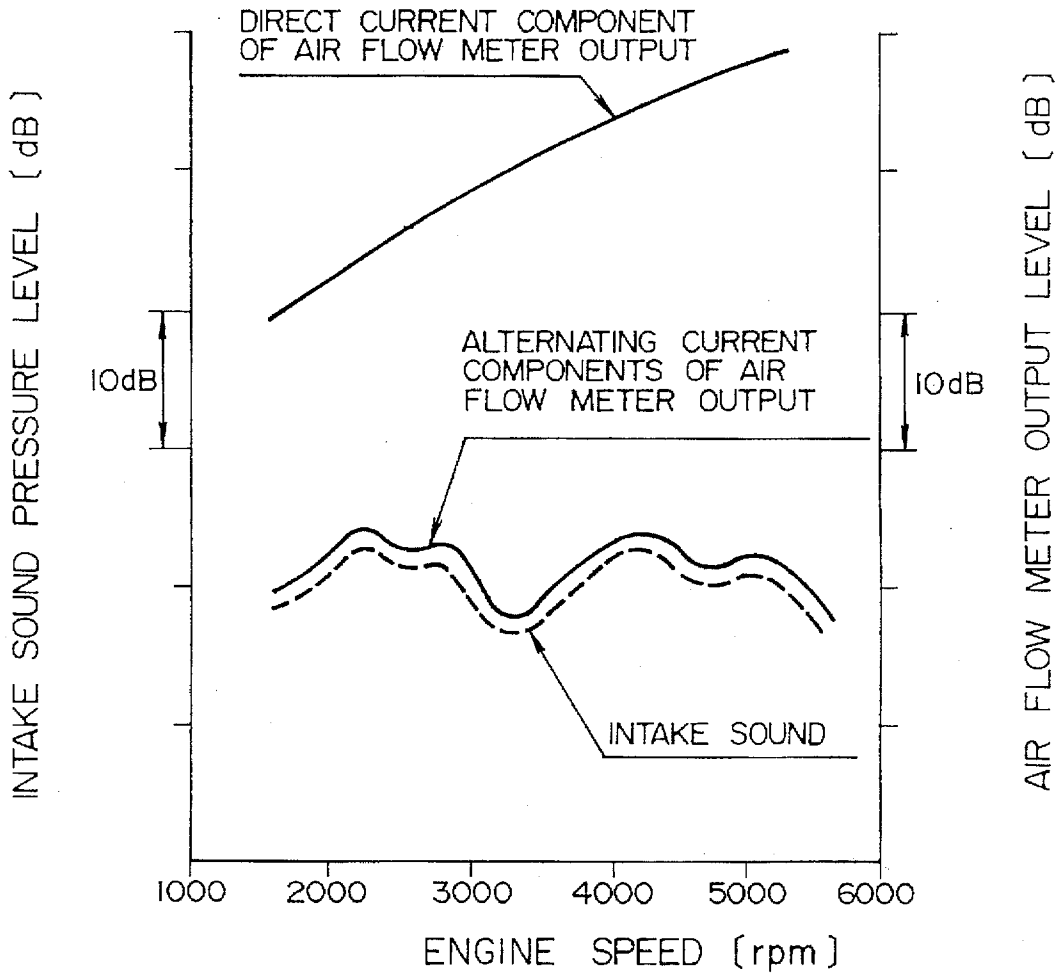
FIG. 20 is a characteristic graph showing changes in the output of the air flow meter with respect to the engine rotating speed.

FIG. 16 shows the configuration of the ECU 54. The signal 53*a* generated by the air flow meter 53 is inputted to a bandpass filter 41 which only extracts alternating current components which are supplied to a CPU 44 through a rectifier circuit 42 as a control signal 42*a*. The signal 53*a* is composed of a direct current component proportional to an intake air amount and alternating current components P proportional to intake air pulsation which are superposed with the direct current component. It can be seen from FIG. 19 that changes in a main component of the alternating current components P along the time is fairly coincident with changes in sound pressure Pa of intake sound. Also, as shown in FIG. 20, changes in both the alternating current component level and the sound pressure level with respect to the engine rotating speed exhibit coincident characteristics.

Figure 21:
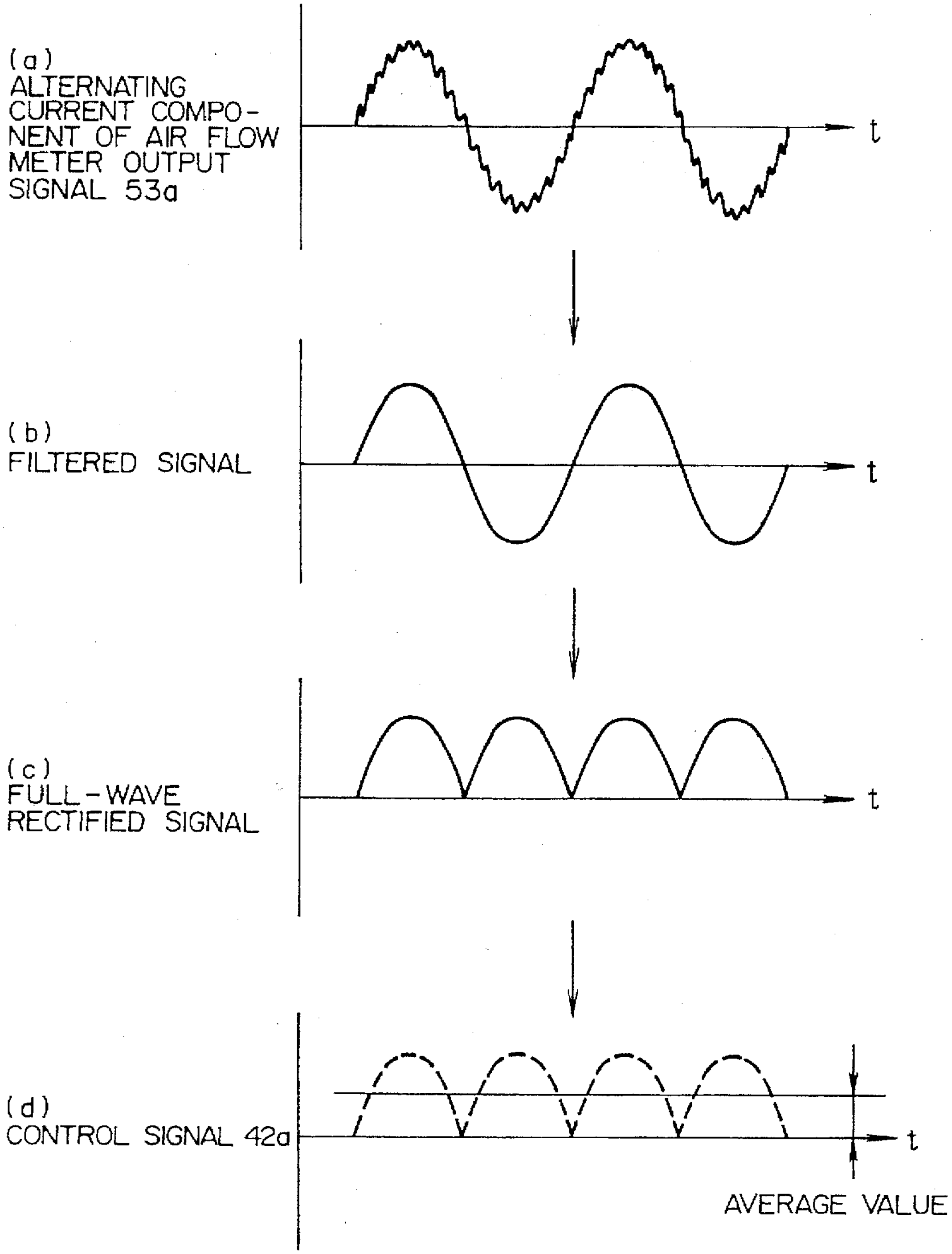
FIG. 21 is a waveform chart showing how a control signal is produced.

The alternating current components of the signal 53*a* from the air flow meter 53 include superposed high frequency components as shown in FIG. 21(*a*) which, however, are removed when the signal 53*a* passes through the bandpass filter 41, thereby leaving only the main component (FIG. 21(*b*)) which is defined by an order corresponding to the number of engine cylinders and the number of cycles (for example, the order is two for a four-cycle four-cylinder engine). The main component is full-wave rectified by a rectifier circuit 42 at the next stage (FIG. 21(*c*)), and then smoothed (FIG. 21(*d*)) to be outputted as the control signal 42*a* indicative of a mean value of the alternating current components. This control signal 42*a* corresponds to intake air pulsation, i.e., the magnitude of intake noise. It will be understood that since exhaust noise generated due to exhaust gas pulsation exhibits a behavior similar to the intake noise, the control signal 42*a* also corresponds to the magnitude of the exhaust noise.

Figure 17:
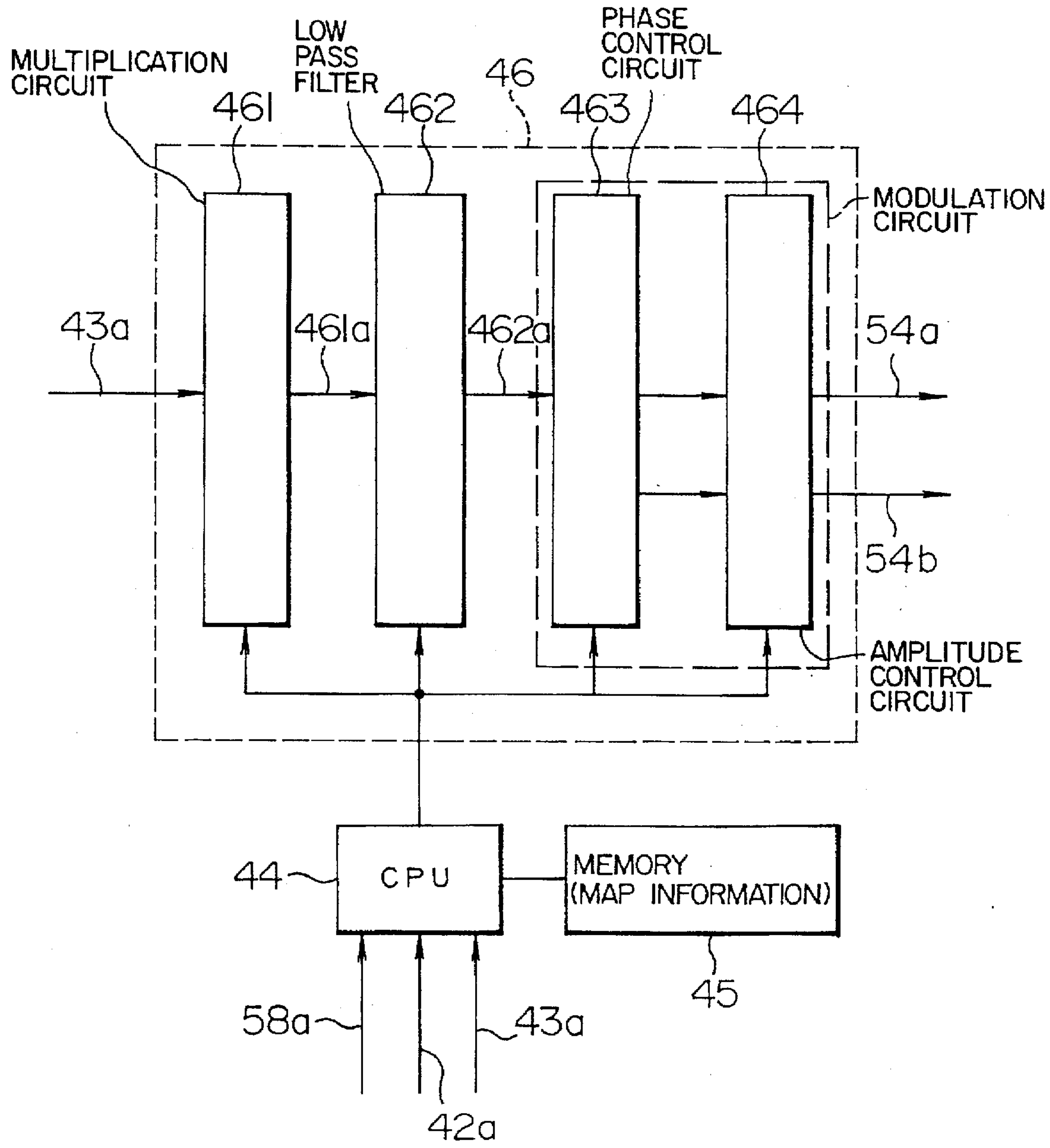
FIG. 17 is a block diagram showing the configuration of a waveform generator circuit.
Figure 18:
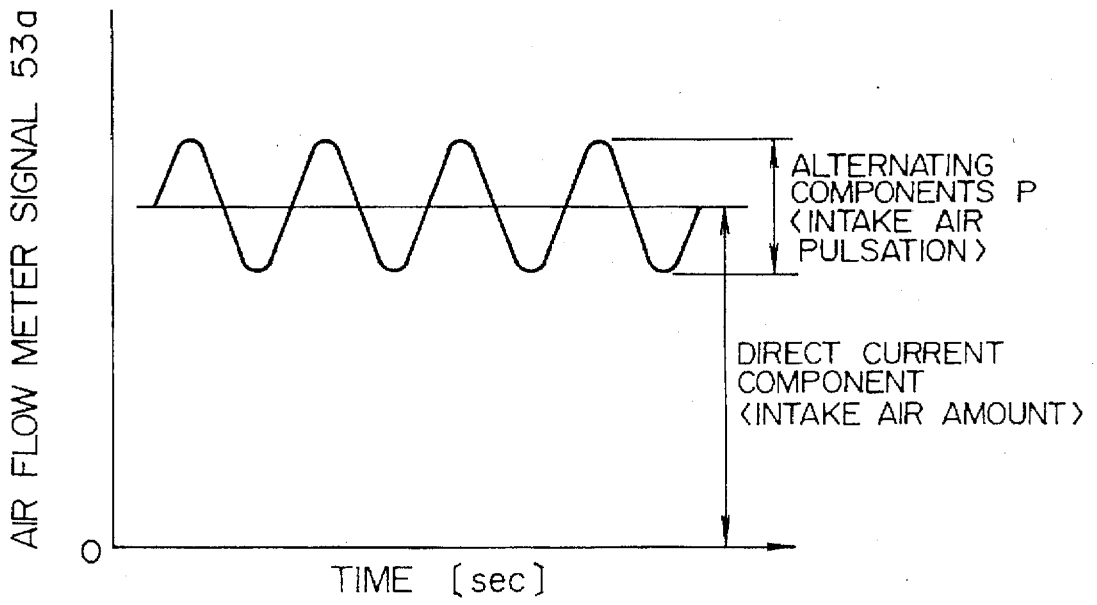
FIG. 18 is a waveform chart showing an output signal of an air flow meter.

The rotation pulse signal 55*a* from the engine rotating speed sensor 55 is inputted to a waveform reshaping circuit 43 (FIG. 16) and reshaped to be a rectangular wave at a TTL level which is supplied to the CPU 44 and a waveform generator circuit 46. The waveform generator circuit 46 is configured as shown in FIG. 17, and comprises a multiplication circuit 461, a low-pass filter 462, a phase control circuit 463, and an amplitude control circuit 464, all of which are serially connected in this order.

The rotation pulse signal 43*a* reshaped by the waveform reshaping circuit 43 is supplied to the multiplication circuit 461. This multiplication circuit 461, in response to a command from the CPU 44, generates a pulse signal at a frequency which is a predetermined multiple of the frequency of the signal 43*a*. In this manner, the multiplication circuit 461 generates a periodic pulse signal 461*a* which has the same frequency, for example, as the main component of the alternating current components included in the signal 53*a* from the air flow meter 53, i.e., the frequency of noise.

The low pass filter 462 at the subsequent stage changes a cut-off frequency thereof by a command from the CPU 44, such that a source driving signal 462*a* in a substantially sine wave shape near the fundamental frequency is extracted from the periodic signal 461*a* including harmonic components and outputted from the low pass filter 462.

Figure 22:
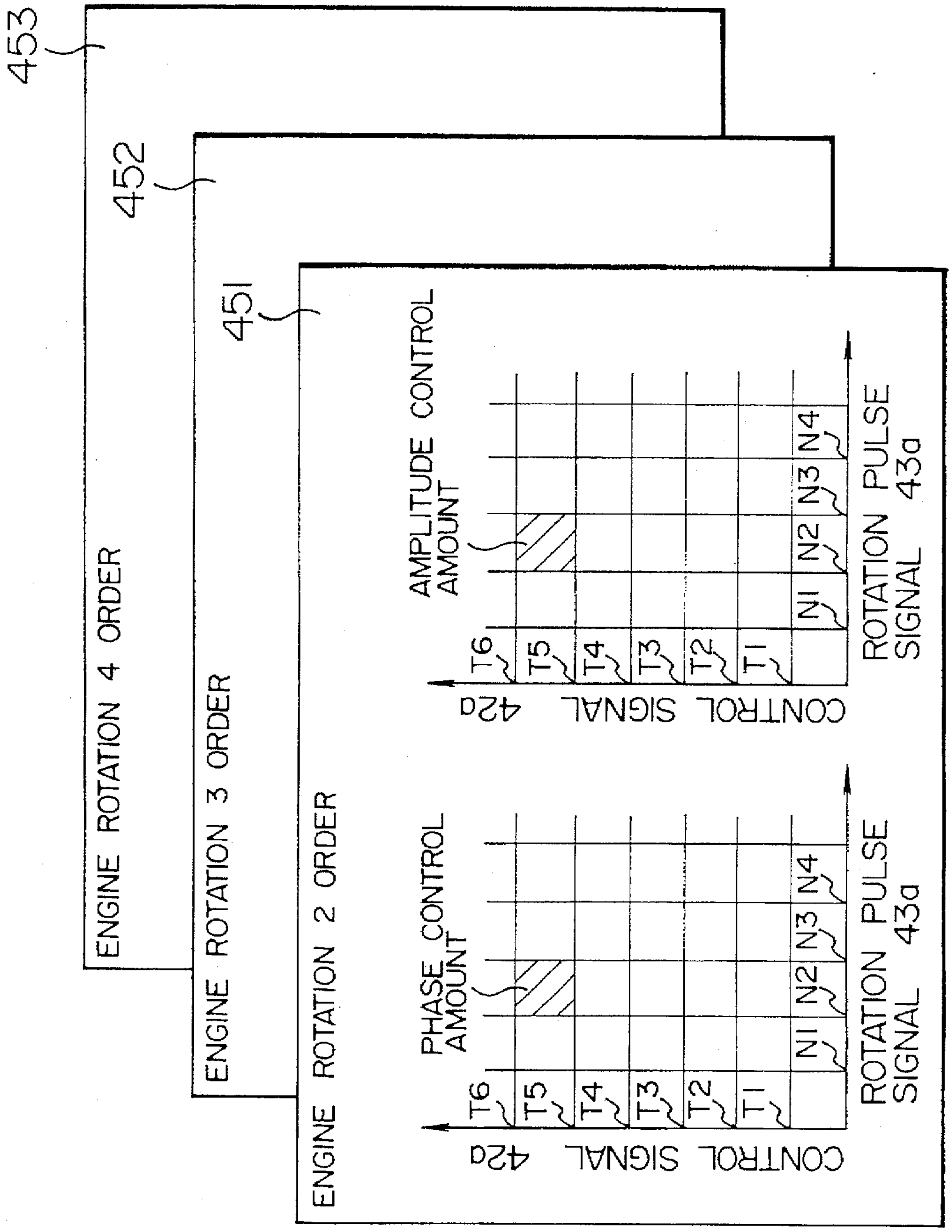
FIG. 22 is a diagram showing a concept of a map.

The source driving signal 462*a*, while passing through the phase control circuit 463 and the amplitude control circuit 464, is modified to modulate its phase and amplitude with respect to the reference position signal 58*a* by predetermined amounts, based on a command from the CPU 44. The modifying amounts of the phase and amplitude have previously been stored in a memory 45 in the form of maps, some examples of which are shown in FIG. 22. As can be seen from FIG. 22, a phase control amount and an amplitude control amount for providing favorable sound damping effects have been empirically determined and set for each combination of predetermined values of the control signal 42*a* generated from the air flow meter output 53*a* and the rotation pulse signal 43*a* indicative of the engine rotating speed (T1, T2, . . . , N1, N2, . . .).

Though illustration is omitted, a plurality of maps 451, 452, 453 are provided corresponding to the respective orders of the engine rotating speed as required, and two sets of these maps are prepared for intake sound and exhaust sound.

The source driving signal 462*a* having its phase and amplitude modified by predetermined amounts by the phase control circuit 463 (FIG. 17) and the amplitude control circuit 464 (FIG. 17) are outputted to intake sound and exhaust sound control speakers 56A, 56B through the respective amplifiers 61, 62 as the driving signals 54*a*, 54*b*. Control sound is generated into the intake tube 52 and the exhaust tube 57 respectively from the speakers 56A, 56B in response to the driving signals. Thus, the control sound from the intake sound control speaker 56A and the control sound from the exhaust sound control speaker 56B, having substantially the same amplitudes and phases different by substantially 180° from each other, cancel or reduce intake sound and exhaust sound, respectively.

In the foregoing manner, the magnitude of the intake air pulsation is predicted from the alternating current components of the output from the air flow meter 53, and the control sound for damping is generated on the basis of the alternating current components and the engine rotating speed, so that intake sound and exhaust sound over wide frequency ranges can be favorably damped promptly in response to even rapid acceleration of the vehicle or the like.

[Tenth Embodiment]

Figure 23:
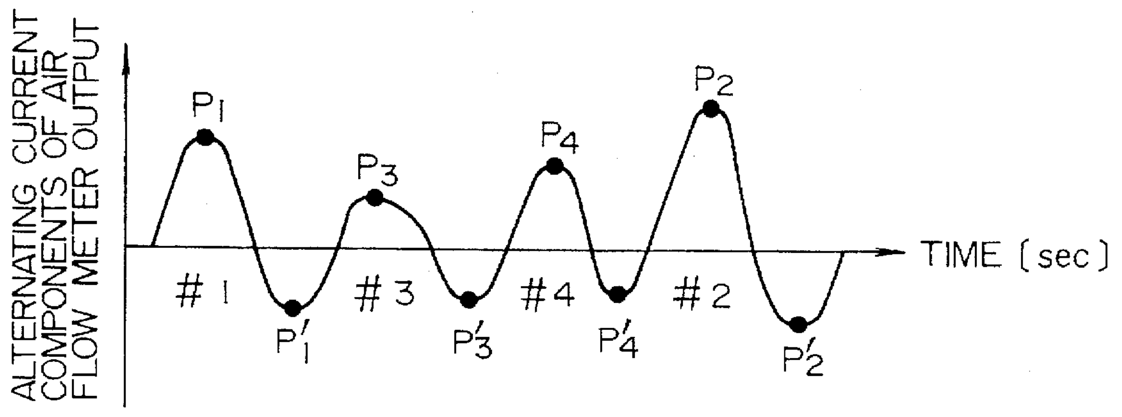
FIG. 23 is a waveform chart showing an output of an air flow meter in another embodiment of the present invention.

As shown in FIG. 23, the alternating current components in the output from the air flow meter 53 may relatively largely vary at peak values P1, P1', P2, P2' . . . for respective cylinders #1, #2, #3, #4 (FIG. 23 shows the case of a four-cylinder engine by way of example). In this event, the peak values for the respective cylinders are averaged in the CPU 44 to derive an average value instead of reshaping the alternating current components by the reshaping circuit 43.

If the peak values for the respective cylinders do not vary so much, a value for any of the cylinders may be taken as being representative of an average value.

Alternatively, instead of calculating an average value of the alternating components for the four cylinders, the noise control may be performed for each cylinder in accordance with the magnitude of pulsation components for each cylinder.

[Eleventh Embodiment]

Figure 24:
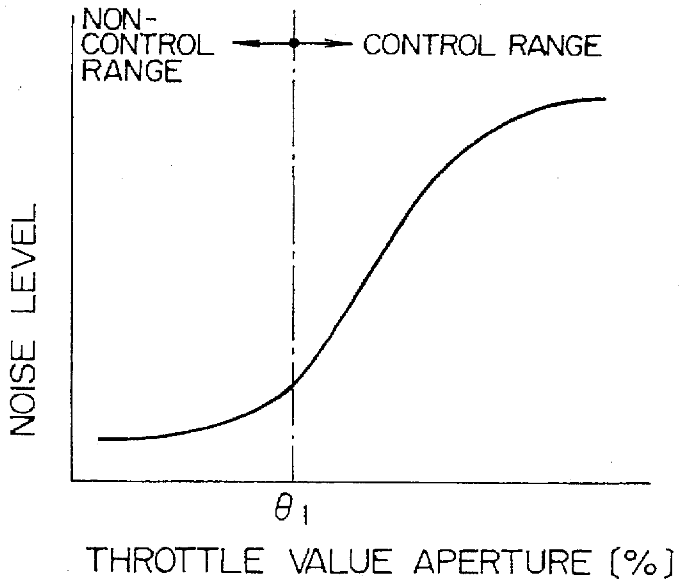
FIG. 24 is a graph showing a control range in a further embodiment of the present invention.
Figure 25:
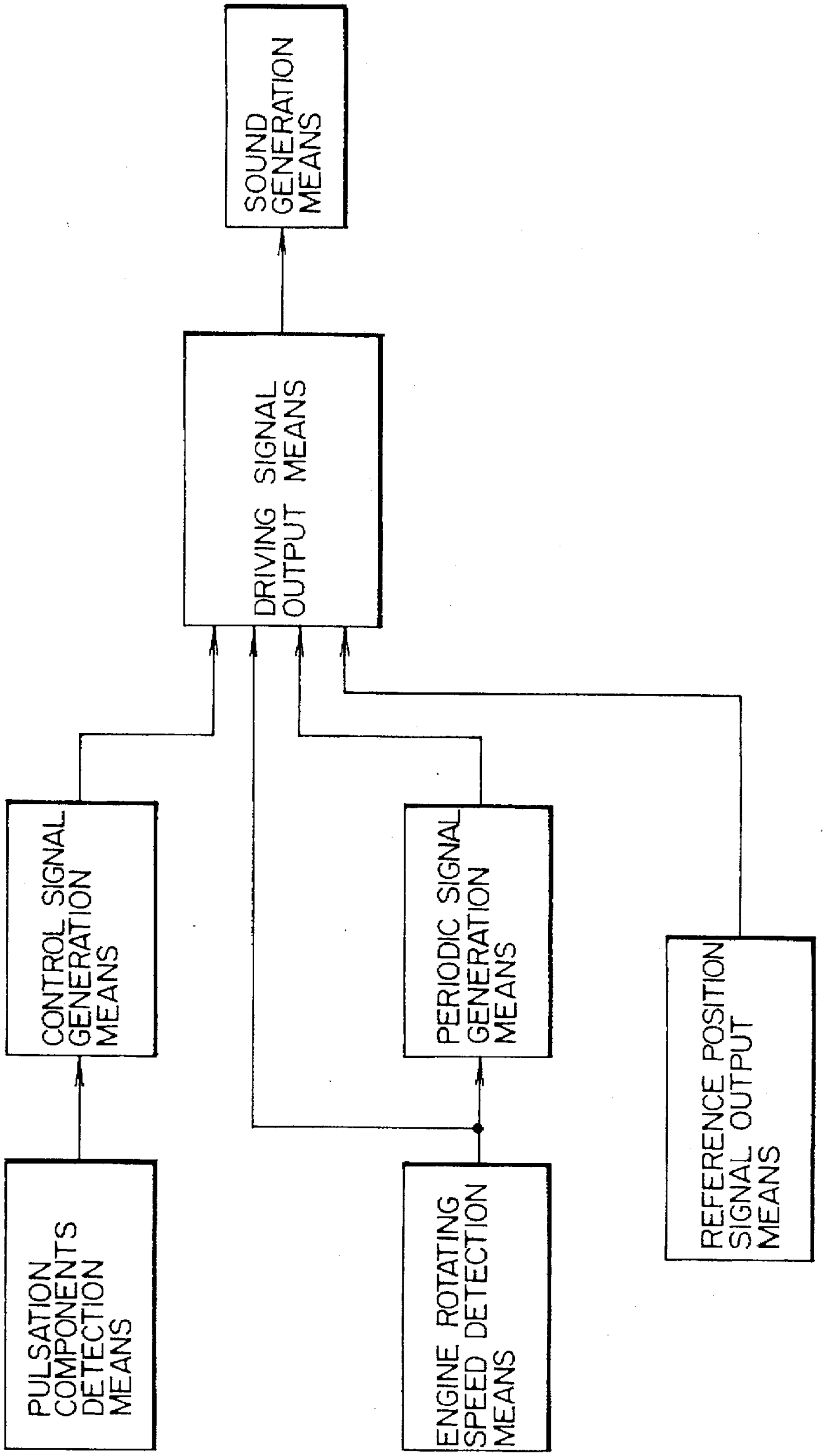
FIG. 25 is a block diagram showing a general configuration of an engine noise control apparatus according to the present invention.

Normally, intake and exhaust noise increases as the throttle valve aperture is larger as shown in FIG. 24. Therefore, the sound damping control may be performed only at the throttle value aperture equal to $\theta_1$ or more, where the noise causes a problem.

[Twelfth Embodiment]

During acceleration of a vehicle, the magnitude of detected pulsation components may exhibit a value smaller than a sound pressure of actual noise due to a response delay of the air flow meter. To solve this problem, when acceleration of the vehicle is detected, the control signal **42*a* generated from the reshaping circuit 42** may be amplified.

[Thirteenth Embodiment]

Even with the same type of engines, errors may occur in the noise control based on previously set map data, due to the difference in layout of the intake system and aging change. Therefore, in consideration of the fact that the pulsation components or alternating components in the output of the air flow meter correspond to an intake sound pressure, learning feedback control may be performed in order to correct map data such that the amplitude control amount is corrected by the magnitude of pulsating intake air, and the phase control amount is corrected by a deviated time of the timing of a peak or bottom of the pulsation components from the timing of the reference position signal. By thus correcting the map data in accordance with the pulsating intake air supplied to the engine to be actually controlled, better noise control can be provided.

Incidentally, since engine noise causes a problem particularly when an engine load is large, the noise control may be started when the alternating current components in the output from the air flow meter show a predetermined value or more.

In the respective embodiments, when an intake tube pressure sensor is provided in place of the air flow meter for EFI, alternating current components in a signal generated by the pressure sensor may also be used, resulting in producing similar effects.

It should be noted that the control sound does not necessarily have a waveform for cancelling or reducing noise, but may have a waveform which modifies noise to a favorable tone.

While the foregoing embodiments have been described for the case where both intake and exhaust noise should be reduced, either of them may be reduced.

Also, in place of speakers, other sound generators using a piezoelectric plate or the like may be used.

As described above, according to the noise control apparatus of the present invention, since pulsation components of engine intake air are detected, and control sound is generated on the basis of the pulsation components and the engine rotating speed, a wide range of intake and exhaust noise can be controlled with a good responsibility.

In the above embodiments, the control sound is generated by detecting an engine load or the intake air supplied to the engine in addition to the engine rotating speed, however, the control sound may be generated on the basis of only the engine rotating speed.

We claim:

1. A sound control apparatus comprising:

engine rotating speed detecting means for detecting a rotating speed of an engine;

engine load detecting means for detecting a load of said engine;

signal generation means for generating an oscillation signal having a frequency which is proportional to said detected engine rotating speed;

memory means including a control map for storing data of phases and amplitudes at a plurality of different addresses, said phases and said amplitudes corresponding to an engine rotating speed and an engine load;

signal modulation means for phase-controlling and amplitude-controlling said oscillation signal in accordance with a phase and an amplitude read from said control map using an address determined by both the detected engine rotating speed and the detected engine load;

control sound generation means for generating control sound in accordance with the signal of said signal modulation means and for supplying said control sound to a propagation path of the sound;

said engine load detecting means comprising a sensor for detecting a signal representing a flow rate of intake air supplied to said engine to be used for engine control, and detection means for detecting pulsation components of intake air flow supplied to said engine on the basis of a signal outputted by said sensor, said detection means detecting said pulsation components of intake air supplied to said engine; and control signal generation means for generating a control signal in accordance with a magnitude of said detected pulsation components of said intake air supplied to said engine, wherein said control signal generation means takes an average of peak values of said pulsation components for cylinders of said engine in a corresponding predetermined period to generate said control signal for each of said cylinders of said engine, and wherein said signal modulation means modulates said oscillation signal on the basis of said each control signal.

2. A sound control apparatus according to claim 1, wherein said signal modulation means outputs said phase-controlled and amplitude-controlled signal as a driving signal when said control signal is larger than a predetermined value.

3. A sound control apparatus according to claim 1, wherein said detection means detects said pulsation com ponents of intake air supplied to said engine using a pressure sensor disposed in a midway of an intake path of said engine.

4. A sound control apparatus according to claim 1, wherein said detection means detects said pulsation components of intake air supplied to said engine using an air flow meter disposed in a midway of an intake path of said engine.

* * * * *